United States Patent
Yang et al.

[11] Patent Number: 5,989,287
[45] Date of Patent: Nov. 23, 1999

[54] VASCULAR GRAFT ASSEMBLIES AND METHODS FOR IMPLANTING SAME

[75] Inventors: Jun Yang; George Guo, both of Dove Canyon, Calif.

[73] Assignee: AV Healing LLC, Dove Canyon, Calif.

[21] Appl. No.: 09/073,743

[22] Filed: May 6, 1998

[51] Int. Cl.⁶ .............................. A61F 2/06; A61F 2/02; A61F 2/04

[52] U.S. Cl. .................. 623/1; 623/11; 623/12; 606/194; 600/36

[58] Field of Search .................. 623/1, 11, 12, 623/66, 900; 606/191, 194; 604/104; 600/36

[56] References Cited

U.S. PATENT DOCUMENTS

| | | |
|---|---|---|
| 2,127,903 | 8/1938 | Bowen . |
| 2,453,056 | 11/1948 | Zack . |
| 3,254,651 | 6/1966 | Collito . |
| 3,496,939 | 2/1970 | Odiaga et al. . |
| 3,626,947 | 12/1971 | Sparks . |
| 3,713,441 | 1/1973 | Thomas . |
| 3,818,511 | 6/1974 | Goldberg et al. . |
| 3,828,764 | 8/1974 | Jones . |
| 4,267,842 | 5/1981 | Archibald . |
| 4,313,231 | 2/1982 | Koyamada . |
| 4,352,358 | 10/1982 | Angelchik . |
| 4,470,415 | 9/1984 | Wozniak . |
| 4,503,568 | 3/1985 | Madras . |
| 4,585,458 | 4/1986 | Kurland . |
| 4,586,504 | 5/1986 | de Medinaceli . |
| 4,728,328 | 3/1988 | Hughes et al. .................. 623/12 |
| 4,743,251 | 5/1988 | Barra .................................. 623/1 |
| 4,856,504 | 8/1989 | Yamamoto et al. . |
| 4,873,975 | 10/1989 | Walsh et al. . |
| 4,883,453 | 11/1989 | Berry et al. . |
| 4,917,087 | 4/1990 | Walsh et al. . |
| 4,938,740 | 7/1990 | Melbin . |
| 5,078,735 | 1/1992 | Mobin-Uddin . |
| 5,084,064 | 1/1992 | Barak et al. . |
| 5,156,619 | 10/1992 | Ehrenfeld . |
| 5,425,739 | 6/1995 | Jessen . |

(List continued on next page.)

FOREIGN PATENT DOCUMENTS

| | | |
|---|---|---|
| 0302088 | 2/1989 | European Pat. Off. . |
| 2676355 | 11/1992 | France . |
| 2269104 | 2/1994 | United Kingdom . |
| WO8204390 | 12/1982 | WIPO . |
| WO9609800 | 4/1996 | WIPO . |
| WO9618360 | 6/1996 | WIPO . |
| WO9731591 | 9/1997 | WIPO . |

OTHER PUBLICATIONS

Madras et al., Anastomotic Hyperplasia, 1981, "Surgery", 922.

Mobin–Uddin et al., Vascular Anastomosis with Mobin–Uddin Vein/Graft Holder, 1986, "Ann Thorac Surg.", 591.

Clark et al., Mismatch of Mechanical Properties As a Cause of Arterial Prosthesis Thrombosis, 1976, "Surgical Forum", 208–209

(List continued on next page.)

*Primary Examiner*—Mickey Yu
*Assistant Examiner*—Dinh X. Nguyen
*Attorney, Agent, or Firm*—Raymond Sun

[57] ABSTRACT

A graft system is provided that includes either a support ring or a support sleeve that is used in providing transitional support to either an end or a side of a graft or a host vessel. The support ring is provided with a generally cylindrical wall and defining a passageway that is adapted for receiving an end of a vein graft or an end of a host vessel. The support ring has a first end and a second end, with the thickness of the wall being greater at the first end than at the second end. The support sleeve is provided with a first side edge, a second side edge, and an opening. The support sleeve surrounds a side opening of a graft or host vessel so that the opening of the support sleeve is aligned with the side opening of the graft or host vessel. The thickness of the support sleeve is greater at the opening than at the first and second side edges.

17 Claims, 6 Drawing Sheets

U.S. PATENT DOCUMENTS

| | | |
|---|---|---|
| 5,456,712 | 10/1995 | Maginot . |
| 5,456,714 | 10/1995 | Owen . |
| 5,486,187 | 1/1996 | Schenck . |
| 5,522,881 | 6/1996 | Lentz . |
| 5,591,226 | 1/1997 | Terotola et al. . |
| 5,609,626 | 3/1997 | Quijano et al. ............................. 623/1 |
| 5,628,782 | 5/1997 | Myers et al. . |
| 5,645,581 | 7/1997 | Zurbrugg .................................... 623/1 |
| 5,665,117 | 9/1997 | Rhodes ........................................ 623/1 |
| 5,667,523 | 9/1997 | Bynon et al. ............................ 606/198 |
| 5,693,088 | 12/1997 | Lazarus ....................................... 623/1 |
| 5,817,100 | 10/1998 | Igaki ........................................ 606/108 |

OTHER PUBLICATIONS

Campbell et al., Vein Grafts for Arterial Repair: their success and reasons for failure, 1981, "Annals of the Royal College of Surgeons of England", vol. 63, 257–260.

DeWeese, Anastomotic Neointimal Fibrous Hyperplasia, 1985, "Complications in Vascular Surgery", 157–170.

Goldman et al., Starting Aspirin Therapy After Operation, 1991, 520–526.

DeWeese et al., Autogenous venous grafts ten years later, 1977, "Surgery" vol. 82, No. 6, 775–784.

Imparato et al., Intimal and neointimal fibrous proliferation causing failure of arterial reconstructions, "Surgery", vol. 72, No. 6, 1007–1017.

Grondin et al., Coronary Artery Bypass Grafting with Saphenous Vein, 1989, "Circulation", vol. 79, No. 6, I–24—I–29.

VASCULAR GRAFT ASSEMBLIES AND METHODS FOR IMPLANTING SAME

BACKGROUND OF THE INVENTION

1. Field of the Invention

The present invention relates generally to vascular grafts and methods of implantation of vascular grafts, and in particular, to graft systems or assemblies for use in grafting and methods for deploying these graft systems in bypass grafting procedures.

2. Description of the Prior Art

Over the past thirty years, a large number of vascular grafts have been surgically implanted in patients to (i) revascularize blood flow from diseased arteries and veins, (ii) to replace the diseased arteries and veins, and (iii) to bypass regions of severe stenosis. These vascular grafts have been provided in the form of autogenous grafts, synthetic grafts, or grafts of biological origins (homogeneous or heterogeneous). Synthetic grafts are generally used for mending large arteries, while autogenous saphenous veins are generally used for arterial reconstruction of smaller vessels (such as in the lower extermities). In aortocoronary bypass, autogenous vein grafts are typically anastomosed proximally to the ascending aorta and distally to the coronary artery downstream from the stenosis.

Occlusion of implanted grafts leading to graft failure is a major problem encountered in all cases. In general, in the case of coronary arterial bypass grafts (CABG), the patency rates of human saphenous vein grafts varies, but by ten years, only fifty percent of such implanted grafts are expected to remain patent, with about half of the patent grafts suffering from severe atherosclerosis. Unfortunately, the patency rate is even lower for grafts used in lower-extremity bypass cases.

The causes of such graft failures can be categorized as intrinsic and extrinsic factors. Intrinsic factors involve the adaptations within the graft wall itself, and intimal hyperplasia and atherosclerosis are two major intrinsic factors associated with post-operative failure of arterial bypass grafts. Extrinsic factors involve physiology related to, but not directly part of, the graft, such as the blood, the arterial bed into which the graft is placed, and the surgical technique.

In CABG applications, early occlusion (i.e., less than one month from the surgical procedure) occurs in about five to fifteen percent of all cases. In fact, graft occlusion within one week of the procedure occurs in about seven to eight percent of the cases. These numbers are significant, and attempts have been made to minimize the percentage of early occlusion cases by (i) utilizing techniques of surgical preparation that preserve a nonthrombogenic endothelium, and (ii) providing an optimal anastomosis.

Optimal anastomosis is especially important to the potential patency of the graft, but a number of factors make it difficult to achieve. For example, the graft opening must be properly sized to prevent kinking at the anastomotic site. Meticulous (i.e., careful) anastomosis is also required for small anastomosis to obtain good patency. However, these procedures may be difficult to accomplish if the vein graft is collapsed. To address this problem, a pickup forceps is typically used to hold the vein opening during aortocoronary and peripheral vascular bypass surgery. However, the forceps may cause endothelial injury and can slip from its position during the anastomosis. Other holding devices (e.g., the Mobin-Uddin vein graft holder) were developed to address the deficiencies of the forceps, but these devices are still not completely satisfactory when used for anastomosis because they may still cause injury to the endothelium, or do not provide satisfactory circumferential support to the vein graft.

Optimal anastomosis should minimize the occurrence of bleeding. In many cases, bleeding can be a problem after completion of the anastomosis. Although a significant etiologic factor for this bleeding is systemic heparinization or an acquired platelet dysfunction associated with cardiopulmonary bypass, the surgical site may also be a contributing factor because of suboptimal surgical techniques used during the anastomosis. The proximal anastomosis of an aortocoronary artery bypass graft is one such potential site. Factors that may contribute to bleeding at this site include the quality of the aorta and implanted saphenous vein, as well as the anastomotic stitch spacing and tension. However, one factor that is particularly troublesome in some cases is that the aortotomy is significantly larger in size than the diameter of the saphenous vein (i.e., there is a size mismatch). In such cases, the wall of the vein becomes stretched and tensioned at the proximal anastomotic site, as shown in FIG. 3B (which is described in greater detail hereinbelow). The size mismatch also results in a tendency for the anastomotic suture to cut through the vein, resulting in bleeding. Additional stitches placed to control this bleeding may result in further tearing of the vein, thereby exacerbating the condition so that the proximal anastomosis becomes a site of major hemorrhage. In addition to the bleeding problems, a mismatch in the size of the aortotomy and the saphenous vein graft may cause the vein to flatten at the site of the anastomosis, thereby impairing blood flow through the graft.

The optimal way to manage this difficult mismatch situation would be to avoid it by appropriately judging the size of the aortotomy. However, it is very difficult to properly predict how much an anastomosed vein graft will expand when subject to arterial pressure. Thus, this mismatch in the size of the aortotomy and the saphenous vein graft will occur in many cases. If significant bleeding results from such a mismatch or other unsatisfactory vein contour, a number of surgical options are available. According to one option, the vein graft can be disconnected from the aortotomy (which is then closed), and the proximal end of the vein graft is refashioned and anastomosed to a more appropriately-sized aortotomy. According to another option, the vein graft can be disconnected from the aortotomy (which is then closed), and the vein is anastomosed in end-to-side manner to another saphenous vein graft that has already been joined to the aorta. Unfortunately, there are potential problems with these two surgical options. An aortotomy, especially an oversized one, can be difficult to close hemostatically. In addition, a direct vein-to-vein anastomosis where one of the veins is markedly narrow may potentially place both grafts at risk for early occlusion. As a result, a third surgical option is to place a partial-thickness stitch circumferentially around the aortotomy. A partial-thickness stitch does not extend entirely through the wall of the aortotomy, and the stitch has to be tied with sufficient tension to reduce the circumference of the aortotomy but without cutting through the aorta. Unfortunately, partial-thickness stitches may cause the layers that make up the aortotomy to separate (known as delamination).

In addition to minimizing bleeding, an optimal anastomosis should also provide (i) proper anastomotic geometry (e.g., opening, inflow and outflow tracts) to ensure a smooth rheologic boundary, and (ii) minimal internal wall stress in connecting vessels or grafts at the anastomotic region.

Regarding proper anastomotic geometry, it is important to note that materials with different mechanical properties (also known as this compliance mismatch), when joined together and placed in a cyclic stress system, exhibit different extensibilities. Compliance mismatch can be defined as the nominal difference in compliance between the blood vessel and a synthetic graft. "Extensibility" describes how much a vessel or a graft expands under arterial pressure. Stress concentrations at or near the site of coaptation can result in marked changes of geometry (e.g., out-of-plane bending, and buckling).

Regarding internal wall stress, it should be noted that compliance mismatches may cause increased stress at the anastomotic sites, as well as create flow disturbances and turbulence. Suture lines can also cause additional local compliance mismatches at the connection of the graft and the vessel, and may affect how stress is transmitted to an anastomotic site. It is believed that compliance mismatches at the interface of the graft and the vessel causes regional hemodynamic disturbances, which result in turbulent blood flow and shear forces that are imparted to adjacent flow surfaces. Such flow disruption may lead to para-anastomotic intimal hyperplasia, anastomotic aneurysms, and the acceleration of downstream atherosclerotic change.

Thus, there still remains a need for a graft assembly or system which promotes optimal anastomosis, which distributes stresses in an optimal manner, which is easy to implant, and which generally minimizes or avoids the problems described hereinabove.

SUMMARY OF THE DISCLOSURE

In order to accomplish the objects of the present invention, the present invention provides a support ring or a support sleeve that is used in providing transitional support to either an end or a side of a graft or a host vessel.

According to one embodiment of the present invention, a support ring is provided having a generally cylindrical wall and defining a passageway that is adapted for receiving an end of a vein graft or an end of a host vessel. The support ring has a first end and a second end, with the thickness of the wall being greater at the first end than at the second end. In one embodiment, the thickness of the wall gradually decreases from the first end of the support ring to the second end of the support ring. The first end of the support ring is disposed at an angle with respect to a longitudinal axis that extends through the passageway.

According to another embodiment of the present invention, a support sleeve is provided having a first side edge, a second side edge, and an opening. The support sleeve surrounds a side opening of a graft or host vessel so that the opening of the support sleeve is aligned with the side opening of the graft or host vessel. The thickness of the support sleeve is greater at the opening than at the first and second side edges. In one embodiment, the thickness of the support sleeve gradually decreases from the opening of the support sleeve to the first and second edges thereof. The support sleeve can also be provided in the form of a sheet having opposing third and fourth edges that are stitched together.

The support rings and support sleeves of the present invention can be made of a material having features or characteristics similar to those of an artery so as to facilitate the close matching of the mechanical properties or extensibilities. For example, the material can be an elastic material having sufficient stiffness so that it will not expand beyond a certain limit.

Thus, the support rings and the support sleeve that are used in the graft systems and methods according to the present invention promote optimal anastomosis by providing external circumferential support to the weaker vessel (i.e., either the vein graft or the diseased artery) at the anastomosis site, and by providing an effective seal for the anastomosis. In addition, the gradually decreasing wall thickness of the support rings and the support sleeve provides a gradually tapering or withdrawing of the support from the anastomotic coaptation.

BRIEF DESCRIPTION OF THE DRAWINGS

FIGS. 1A–1C illustrate a vein graft system and method according to a first embodiment of the present invention shown in use to connect an aorta with a coronary artery in an end-to-side manner;

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

The present invention provides graft systems and methods for use in connecting blood vessels with the aorta or other blood vessels. The graft systems of the present invention promote optimal anastomosis by providing support rings, sheets or sleeves that provide an optimal transition at the anastomotic sites between the graft and the host aorta or vessel. These optimal transitions are created by providing support for the weaker connecting vessel at the anastomotic coaptation. Even though the drawings and embodiments illustrated herein are described in connection with CABG applications, the principles, systems and methods of the present invention can also be applied to other similar applications, such as in the peripherals (such as the extremities) and for pulmonary applications.

Figure 1A:
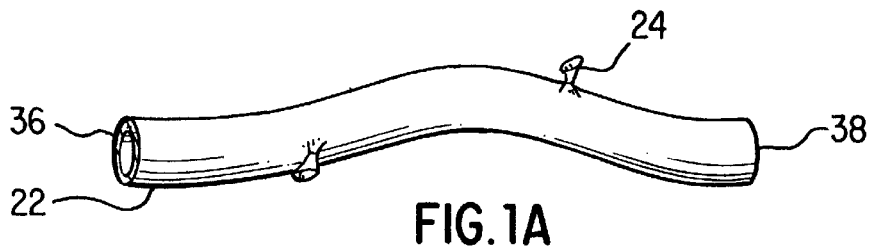
Figure 1B:
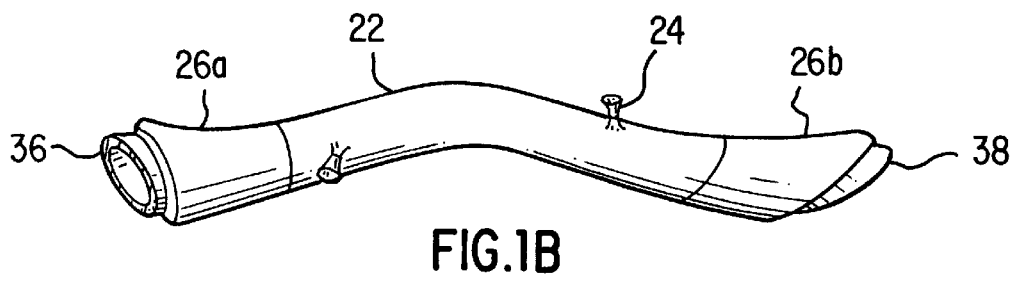

FIGS. 1A–1C and 2A–2B illustrate a system 20 according to one embodiment of the present invention. The system 20 uses a patient's own vein 22, such as a saphenous vein, as the graft. Referring to FIG. 1A, the vein 22 is harvested from the patient using known surgical techniques. The collaterals or side branches 24 of the vein 22 are tied off, and the vein 22 can be washed with saline and, optionally, with pharmaceutical reagents (such as heparin). Then, as shown in FIG. 1B, a first support ring 26a is slid over the first end 36 of the vein 22, and a second support ring 26b is slid over the second end 38 of the vein 22. The support rings 26a, 26b function to provide support for the weaker connecting vessel (in this case, the vein 22) at the anastomotic coaptation, and is described in greater detail below.

Figure 2A:
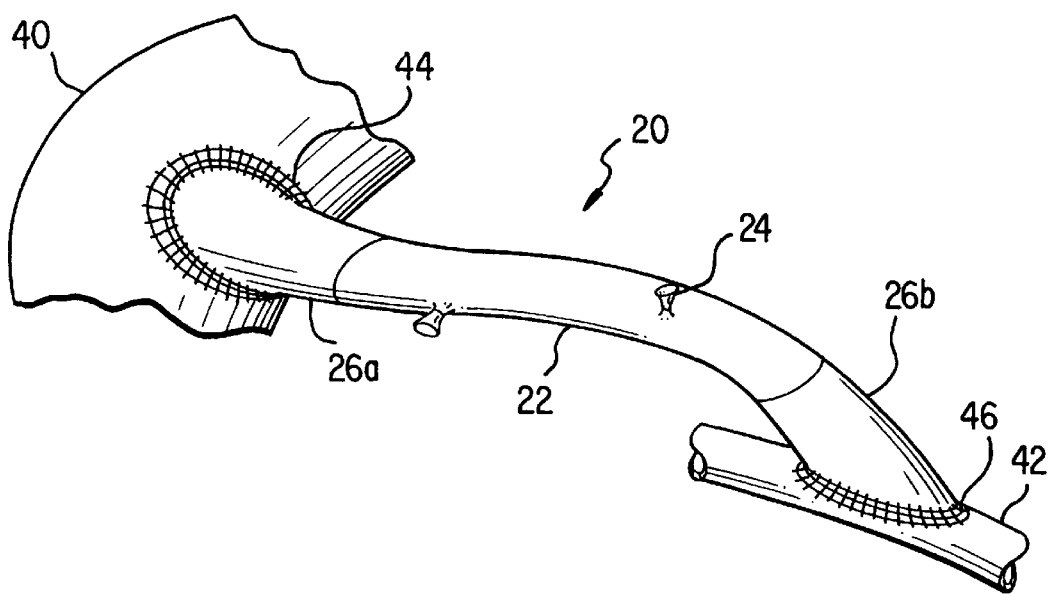
FIG. 2A is a perspective view of the support ring of the graft system of FIGS. 1A–1C.
Figure 2A:
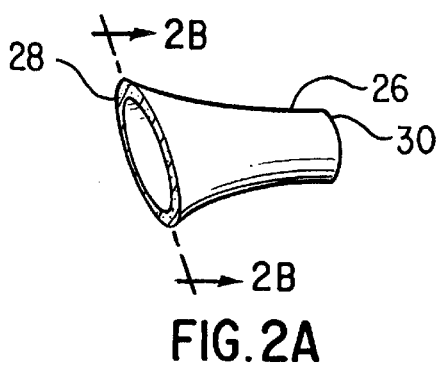
Figure 2B:
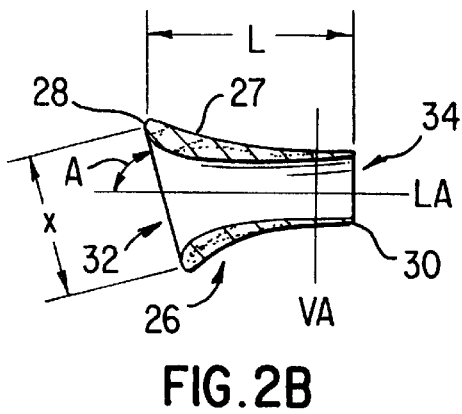
FIG. 2B is a longitudinal cross-sectional view of the support ring of FIG. 2A.

Each support ring 26a, 26b can be identical in structure, and is illustrated in greater detail using the common designation 26 in FIGS. 2A and 2B. The support ring 26 has a generally cylindrical wall 27, and is formed by an oblique cone shaped sleeve having a gradually reduced wall thickness, with the material and wall thickness selected to optimize the anastomosis that is to be effected. In other words, it is desired that the wall thickness and material of the support ring 26 be selected so that the support ring 26 can act as a transition that enables the mechanical properties of the vein graft 22 and the artery or aorta to be anastomosed to be matched as closely as possible.

In particular, the combination of the material and the configuration of the support ring 26 at the first end 28 (described below) of the support ring 26 should preferably have features or characteristics similar to those of an artery so as to facilitate the close matching of the mechanical properties or extensibilities. It is believed that such close matching will promote the likelihood of obtaining an optimal anastomosis. In this regard, the material should be sufficiently elastic to allow the support ring 26 at its first end 28 to expand under arterial pressure, just as an artery would, so that the support ring 26 would expand along with the artery and vein graft 22 at the site of the anastomosis. In addition, the material should exhibit non-linear expansion properties. In other words, the material should have sufficient stiffness so that it will not expand beyond a certain limit. Moreover, the material should preferably be nonresorbable or slowly resorbable in the receiving host by the surrounding tissue in which it is implanted.

Materials that exhibit the above-referenced features or characteristics include synthetic or natural elastomers (e.g., silicone elastomers, silicone rubbers, polyurethanes). Other types of materials that may be suitable include a fiber reinforced composite material containing an elastomeric matrix with a fabric mesh, or a fabric mesh with elastic textile configuration embedded in a flexible non-elastomeric matrix. It is also possible to use elastic materials with biological origins containing collagen and elastin network, such as a mammalian artery.

The support ring 26 has opposing first and second ends 28 and 30, respectively, defining first and second openings 32 and 34, respectively. The first opening 32 has a greater diameter than the second opening 34, and the thickness of wall 27 is greatest at the first end 28 and gradually decreases to the smallest thickness at the second end 30. The decrease in the wall thickness from the first end 28 to the second end 30 can be linear, or can be expressed in a more complex form, such as exponential or parabolic. The longitudinal cross-section of the wall 27 may be triangular or shaped as an airfoil or other shape providing a smooth transient surface.

The inner diameter of the support ring 26 along its longitudinal length is preferably generally consistent throughout, and is slightly larger than the outer diameter of the vein graft 22 over which it is to be disposed. When the support ring 26 is placed longitudinally along a horizontal axis LA, the first end 28 is disposed at an angle A with respect to the horizontal axis LA. This angle A can be referred to as the anastomotic surface angle, and preferably ranges from 30 to 90 degrees relative to the horizontal axis LA if the first end 28 is intended to be anastomosed to an artery or in a side-to-end manner, as described below. The second end 30 is disposed generally perpendicular (i.e., at about 90 degrees) to the horizontal axis LA.

FIG. 1C illustrates how the graft assembly 20 is used to accomplish bypass grafting between the aorta 40 and a distal coronary artery 42 of a patient. Referring back to FIG. 1B, the support rings 26a, 26b are secured to the first and second ends 36 and 38, respectively, of the vein 22 by sliding the rings 26a, 26b over the ends 36 and 38, respectively, in a manner so that the first larger ends 28 of the rings 26a, 26b face the ends 36, 38 of the vein 22, and then everting the ends 36, 38 over the first ends 28 of the rings 26a, 26b and applying a stitching. As an alternative, the ends 36, 38 of the vein 22 do not need to be everted, but can be merely stitched to the first ends 28 of the rings 26a, 26b. The combined first end 28 of the first support ring 26a and the first end 36 of the vein 22 are anastomosed in side-to-end manner to the aorta 40 by stitches 44. The combined first end 28 of the second support ring 26b and the second end 38 of the vein 22 are anastomosed in end-to-side manner to the artery 42 by another set of stitches 46. The second ends 30 of the rings 26 do not need to be connected to the vein 22.

The cross-section of the first opening 32 of the support ring 26 can be either circular or oval, depending upon the type, location, size and shape of the artery or aorta to be anastomosed. In general, the first opening 32 is preferably circular in the cases (i) where the support ring 26 is to be anastomosed in a side-to-end manner, at an almost perpendicular orientation, to the aorta or vessel, or (ii) where the support ring 26 is to be anastomosed in an end-to-end manner to the vessel. In contrast, the first opening 32 is preferably oval in the cases (i) where the support ring 26 is to be anastomosed in a end-to-side manner, at an angled (but other than perpendicular) orientation, to the aorta (such as 40) or vessel, or (ii) where it is desired to increase the circumference of the anastomosis (since an oval has a greater circumference than a circle), or (iii) where the artery or vessel has a thin profile (i.e., small diameter) which is better suited to a thinner anastomotic opening provided by an oval configuration, or (iv) for side-to-side anastomosis. Referring back to FIGS. 1A–1C, the first opening 32 of the first support ring 26a can be circular because the first opening 32 is generally perpendicular to the aorta 40, and because the first support ring 26a is used in anastomosing a larger artery (such as the aorta 40). The first opening 32 of the second support ring 26b should be generally oval since it is anastomosed in end-to-side manner to a relatively thin-profile artery 42. In addition, the short axis y (not shown) or width of the oval opening 32 of the second support ring 26b is designed to match the shape of the opening of the artery 42. The long axis x or height is a function of the ratio x/y, which represents the ratio of the long axis x over the short axis y. Thus, for a circular opening, x and y will be the same. The length L of each support ring 26 can be determined by the ratio L/ID, which is the ratio between the length L and the internal diameter ID (not shown) of the ring 26 at the second end 30. If the cross-section of the ring 26 is oval, then the ratio is preferably 2L/(x+y). The range of the ratios x/y and 2L/(x+y) can range from 1 to 5. For example, a smaller ratio results in a shorter length L for the support ring 26, thereby providing a more abrupt transition, and is generally preferred for end-to-end anastomosis, or in circumstances where a shorter support ring 26 is required, such as where the vein graft 22 is short. Conversely, a larger ratio results in a greater length L for the support ring 26, thereby providing a more consistent and smoother transition, and is generally preferred for side-to-end anastomosis (e.g., at the anastomosis between aorta 40 and the end 36 of vein graft 22 in FIG. 1C).

Thus, the graft system 20 provides a bypass graft in the form of a vein 22 having its opposite, weak, ends 36 and 38 supported by support rings 26a and 26b, respectively, at the anastomotic sites. The gradual decreasing thickness of the wall 27 provides the strongest support at the first end 28, where the wall 27 has the greatest thickness, and also provides a gradually increasing flexibility (i.e., as the thickness decreases) from the location of the stitches 44 to the uncovered portion of the vein 22. As a result, the extensibility of the combined first end 28 of the support ring 26 and the end 36 or 38 of the vein 22 comes close to matching the extensibility of the aorta 40 or artery 42 to which it is to be anastomosed. Similarly, the extensibility of the thin second end 30 of the support ring 26 comes close to matching the extensibility of the uncovered portion of the vein 22. As described above, the choice of materials for the support rings 26a, 26b further promotes this matching of the extensibilities.

Figure 3A:
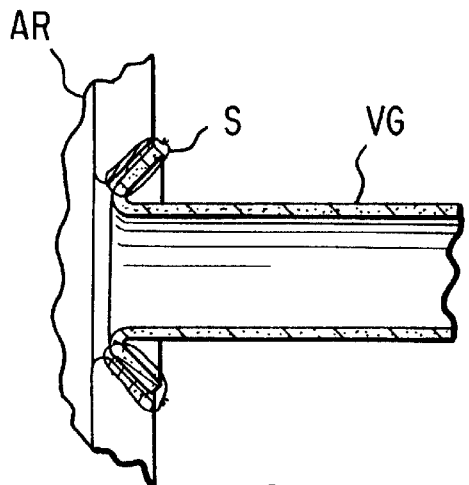
FIG. 3A is a longitudinal cross-sectional view illustrating a conventional end-to-side anastomosis when there is no blood flow therethrough.
Figure 4A:
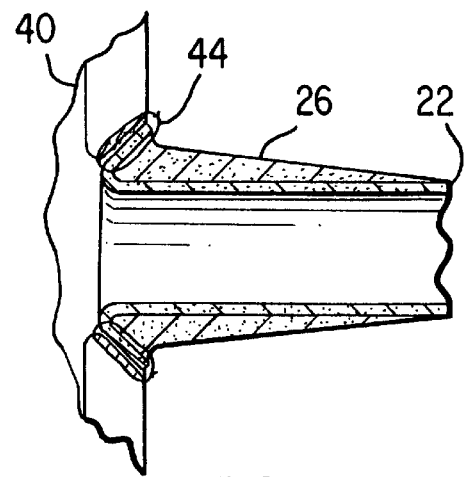
FIG. 4A is a longitudinal cross-sectional view illustrating an end-to-side anastomosis accomplished using the graft system and method of FIGS. 1A–1C when there is no blood flow therethrough.
Figure 3B:
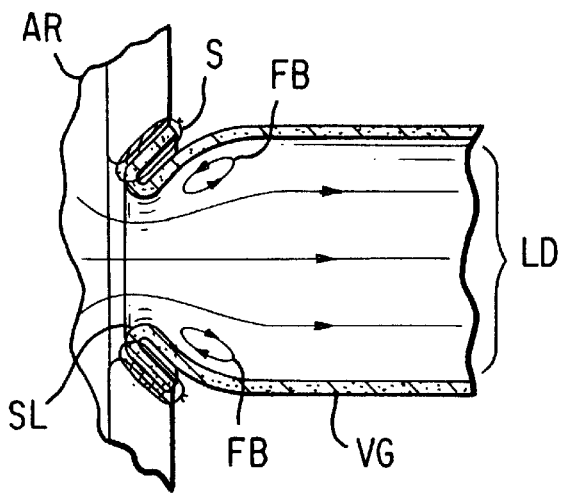
FIG. 3B is a longitudinal cross-sectional view illustrating the end-to-side anastomosis of FIG. 3A when subject to arterial pressure.
Figure 4B:
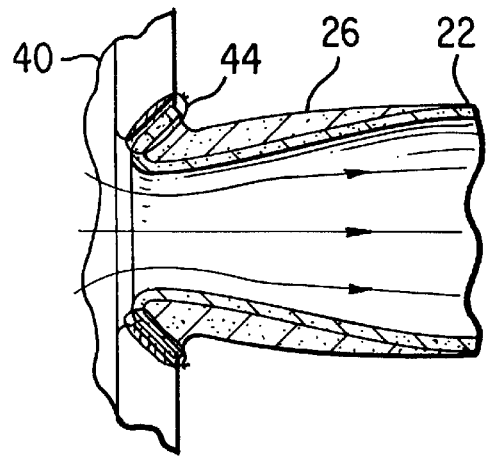
FIG. 4B is a longitudinal cross-sectional view illustrating the end-to-side anastomosis of FIG. 4A when subject to arterial pressure.

In addition, the graft assembly 20 minimizes overstretching, and reduces the stress concentration, of the wall of the vein graft 22. This is illustrated more clearly in FIGS. 3–4. First, FIG. 3A illustrates a conventional vein graft VG that is anastomosed to an artery AR by stitches S at zero mmHg of pressure (i.e., no arterial blood flow). When this vein graft VG is in use after implantation inside a human body, it will experience arterial pressure of about 70–140 mmHg. As illustrated in FIG. 3B, this pressure will cause the vein graft VG to bend (see bend location SL) to assume a larger diameter LD, thereby increasing the stress concentration of the venous wall of the vein graft VG at the bend location SL and creating a blood flow boundary FB separation at the site of the anastomosis. On the other hand, the smooth transition provided by the support rings 26 in the graft assembly 20 of the present invention minimizes the bending and stress concentration of the wall 27 of the vein graft 22, as shown in FIGS. 4A and 4B. In addition, the gradually decreasing thickness of the wall 27 of the support rings 26 provides a smooth divergent transition which controls most flow boundary separations that may be present downstream from the anastomosis sites.

Figure 5A:
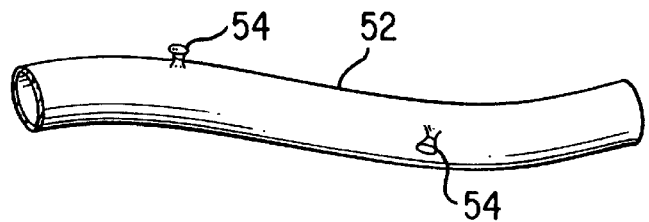
FIGS. 5A–5D illustrate a vein graft system and method according to a second embodiment of the present invention shown in use to connect two coronary arteries in an end-to-end manner.
Figure 5B:
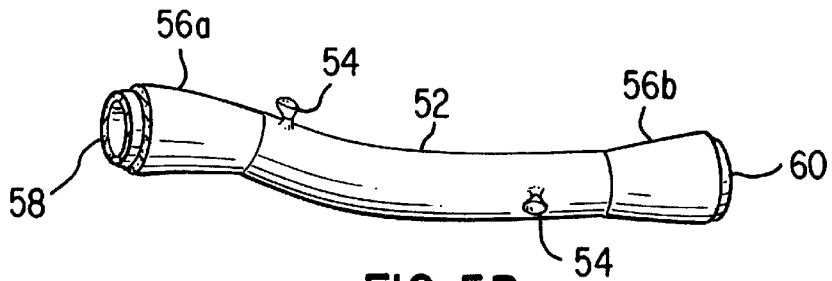
Figure 5C:
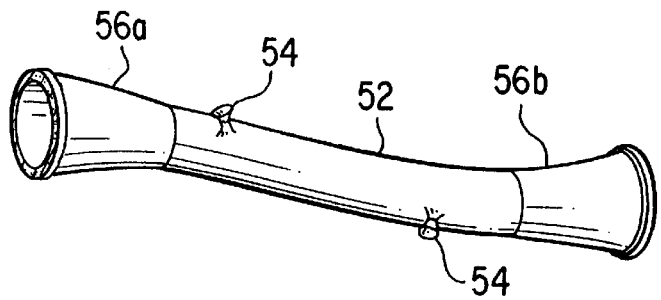

FIGS. 5A–5D and 6A–6B illustrate another system according to the present invention, in which a vein graft 52 is used to connect two coronary arteries in end-to-end manner. The system 50 again uses a patient's own vein 52, such as a saphenous vein, as the graft. Referring to FIG. 5A, the vein 52 is harvested from the patient and prepared in the same manner as the vein 22 prior to implantation. Then, as shown in FIG. 5B, a first support ring 56a is slid over the first end 58 of the vein 52, and a second support ring 56b is slid over the second end 60 of the vein 52. The support rings 56a, 56b function to provide support for the weaker connecting vessel (in this case, the vein 52) at the anastomotic coaptation.

Each support ring 56a, 56b may be identical, and is illustrated in greater detail using the common designation 56 in FIGS. 2A and 2B. The characteristics, materials and features of the support ring 56 are essentially the same as those described above for the support rings 26, except that the wall 57 of the support ring 56 has a tapered conical structure, as opposed to the oblique cone shape of the wall 27. The support ring 56 has opposing first and second ends 62 and 64 that define first and second openings 66 and 68, respectively. The first opening 66 has a greater diameter than the second opening 68, and the thickness of wall 57 is greatest at the first end 62 and gradually decreases, in a generally linear manner, to the smallest thickness at the second end 64. The inner diameter of the support ring 56 along its longitudinal length is preferably consistent throughout, and is slightly larger than the outer diameter of the vein graft 22 over which it is to be disposed. When the support ring 56 is placed longitudinally along a horizontal axis LA, the first end 62 and second end 64 are disposed generally perpendicular with respect to the horizontal axis LA.

Figure 5D:
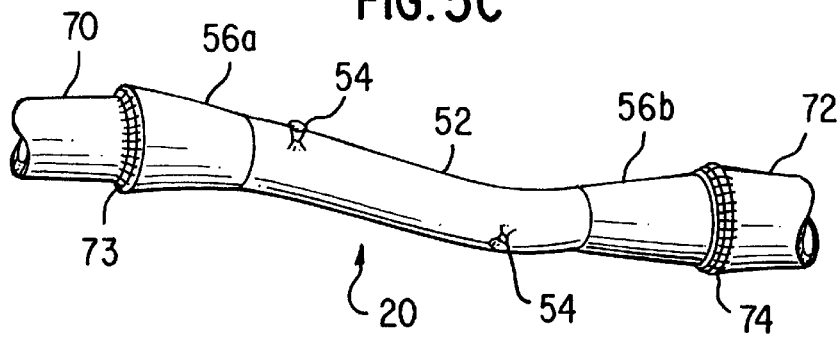
Figure 6A:
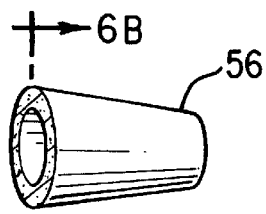
FIG. 6A is a perspective view of the support ring of the graft system of FIGS. 5A–5D.
Figure 6B:
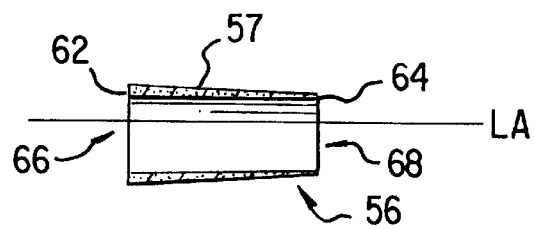
FIG. 6B is a longitudinal cross-sectional view of the support ring of FIG. 6A.

FIG. 5D illustrates how the graft system is used to connect two coronary arteries 70 and 72 in end-to-end manner. Referring back to FIG. 5C, the support rings 56a, 56b are secured to the first and second ends 58 and 60, respectively, of the vein 52 by sliding the rings 56a, 56b over the ends 58 and 60, respectively, in a manner so that the first larger end 62 of the rings 56a, 56b face the outward ends 58, 60 of the vein 52. The ends 58, 60 can then be everted over the first ends 62 of the rings 56a, 56b and stitched, or just merely stitched to the ends 62 without any everting. The combined first end 62 of the first support ring 56a and the first end 58 of the vein 52 are anastomosed to a first coronary artery 70 by stitches 73. The combined first end 62 of the second support ring 56b and the second end 60 of the vein 52 are anastomosed to a second coronary artery 72 by another set of stitches 74.

As with the support rings 26, the cross-section of the first opening 66 of the support ring 56 can be either circular or oval, with the same principles explained above being applicable as well.

Thus, the graft assembly 50 enjoys the same benefits as the graft assembly 20 described above, in which the opposite, weak, ends 58 and 60 of the vein 52 are supported by support rings 56a and 56b, respectively, providing an optimal transition at the anastomosis sites.

Figure 7A:
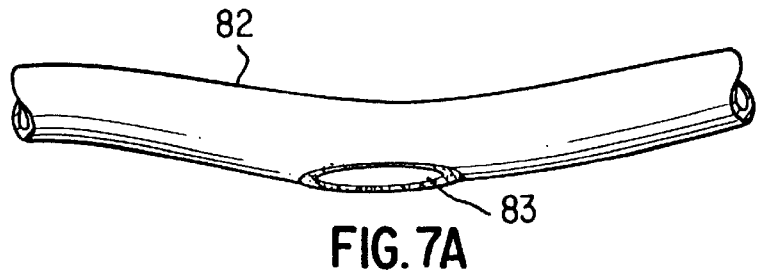
FIGS. 7A–7C illustrate a graft system and method according to a third embodiment of the present invention shown in use to connect a vein graft to a coronary artery in a side-to-side manner.
Figure 7B:
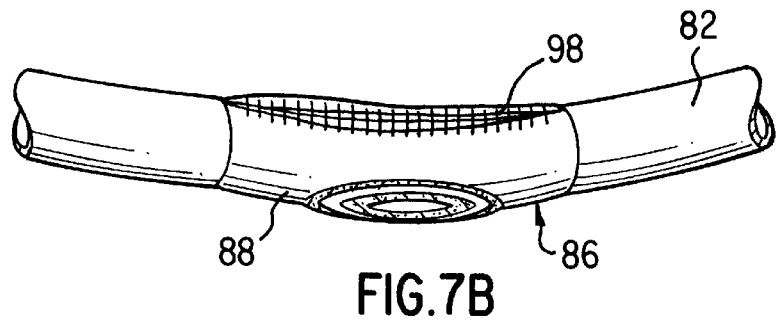

FIGS. 7A–7C and 8A–8B illustrate another system 80 according to the present invention. The system 80 uses a patient's own vein 82, such as a saphenous vein, as the graft for side-to-side anastomosis with an artery. Referring to FIG. 7A, the vein 82 is harvested from the patient and prepared in the same manner as for vein 22. The vein 82 has a side opening 83 for anastomosis to a side opening in an artery 96. Next, as shown in FIG. 7B, a support sleeve 86 is slid over the vein 82 so that a side opening 90 of the support sleeve 86 is aligned with the opening 83 in the vein 82. The support sleeve 86 functions to provide transitional support for the vein 82 and the artery 96 at the anastomosis.

Figure 8A:
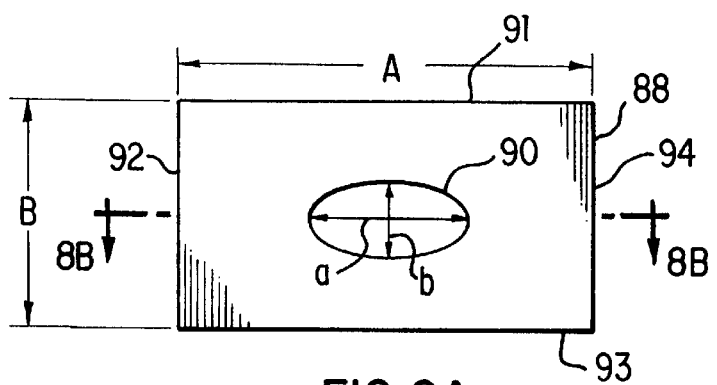
FIG. 8A is a top plan view of a support sheet of the graft system of FIGS. 7A–7C.
Figure 8B:
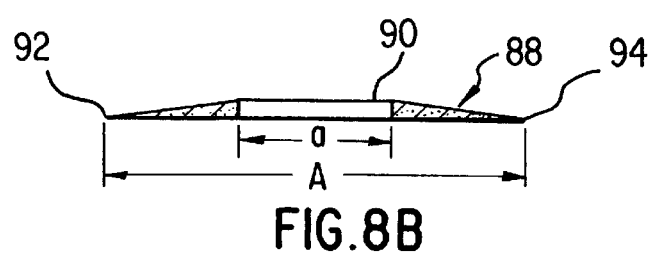
FIG. 8B is a longitudinal cross-sectional view of the support sheet of FIG. 8A.

The support sleeve 86 is illustrated in greater detail in FIGS. 8A and 8B. FIG. 8A illustrates the sleeve 86 in the form of a rectangular sheet 88 having opposite end edges 91 and 93 that can be sutured to form the sleeve 86. When the edges 91 and 93 are sutured, the sleeve 86 has a generally cylindrical configuration (see FIG. 7B) that is adapted to correspond to the configuration and dimension of the vein graft 82. To fit the vein graft 82 inside the sleeve 86, the width B of the sheet 88 should be slightly greater than the circumference of the vein 82 to allow sufficient room for the provision of a suture line 98 that connects edges 91 and 93. In addition, the length A of the sheet 88 can be determined according to a ratio A/B, with the ratio A/B ranging from 1 to 10. As with the ratios described above, a smaller ratio means that the size of the sleeve 86 is smaller, thereby providing a more abrupt transition, and is generally preferred for situations where the physiology requires a smaller sleeve, such as where there is a bifurcation or bend near the anastomotic site. Conversely, a larger ratio results in a larger sleeve 86, thereby providing a more consistent and smoother transition, and is generally preferred for most applications.

The sheet 88 has an opening 90 that is adapted to be aligned with the opening 83 of the vein 82. The openings 83 and 90 are preferably configured to match the artery 96 to be anastomosed. In this embodiment, both openings 83 and 90 are illustrated as being oval in configuration because (i) it is desired to increase the circumference of the opening, (ii) of the smaller profile of the artery 96, and (iii) the anastomosis is side-to-side. The opening 90 also has a short axis b that is close to the outer diameter of the artery 96, and a long axis a that can be determined according to a ratio a/b, with the ratio a/b ranging from 1 to 5. The significance of this ratio a/b and its related principles are similar to those for the ratios x/y and 2L/(x+y) described above. Finally, the openings 83 and 90 can assume any shape and size, except that the shapes and sizes should be closely matched.

The sheet 88 has a wall thickness that is greatest at the central portion at the opening 90, and that gradually decreases in a radial manner to the edges 91, 92, 93, 94 of the sheet 88 where the wall thickness is the smallest. The gradual reduction in wall thickness of the sheet 88 can be linear, or can be expressed in a more complex form, such as exponential or parabolic. The wall thickness and material of the sheet 88 are selected to optimize the anastomosis that is to be effected. In other words, it is desired that the wall thickness and material of the sheet 88 at the opening 90 be selected so that the sheet 88 can act as a transition that enables the extensibilities of the vein graft 82 and the artery to be anastomosed to be matched as closely as possible. In this regard, the material of the sheet 88 may be same as those materials described above for the support ring 26.

Figure 7C:
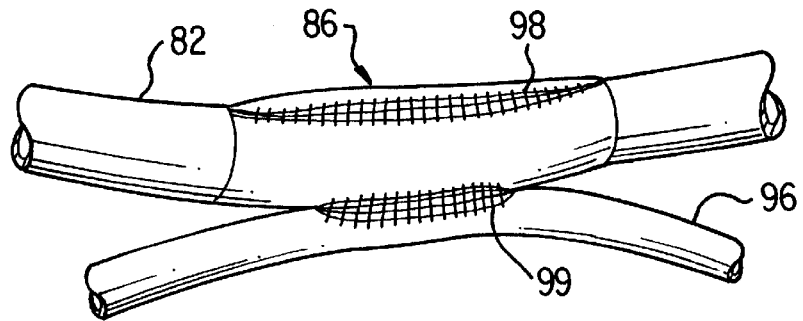

FIG. 7C illustrates how the graft assembly 80 is used for side-to-side anastomosis of the vein graft 82 and an artery 96. Referring back to FIG. 7B, the support sleeve 86 is first secured to the vein graft 82 by stitching. During this step, the support sleeve 86 can be provided in the form of the sheet 88 and then its edges 91 and 93 stitched to form the sleeve. Alternatively, the support sleeve 86 can be provided in a fully assembled generally tubular configuration and slid over the vein graft 82. The aligned openings 90 and 83 are then aligned with a side opening in the artery 96 and anastomosed by stitches 99. Thus, the support sleeve 86 provides support at the anastomosis site, as well as a transition at the anastomosis site between the sides of the vein graft 82 and the artery 96 that promotes the matching of the extensibilities of the vein graft 82 and the artery 96.

Figure 9:
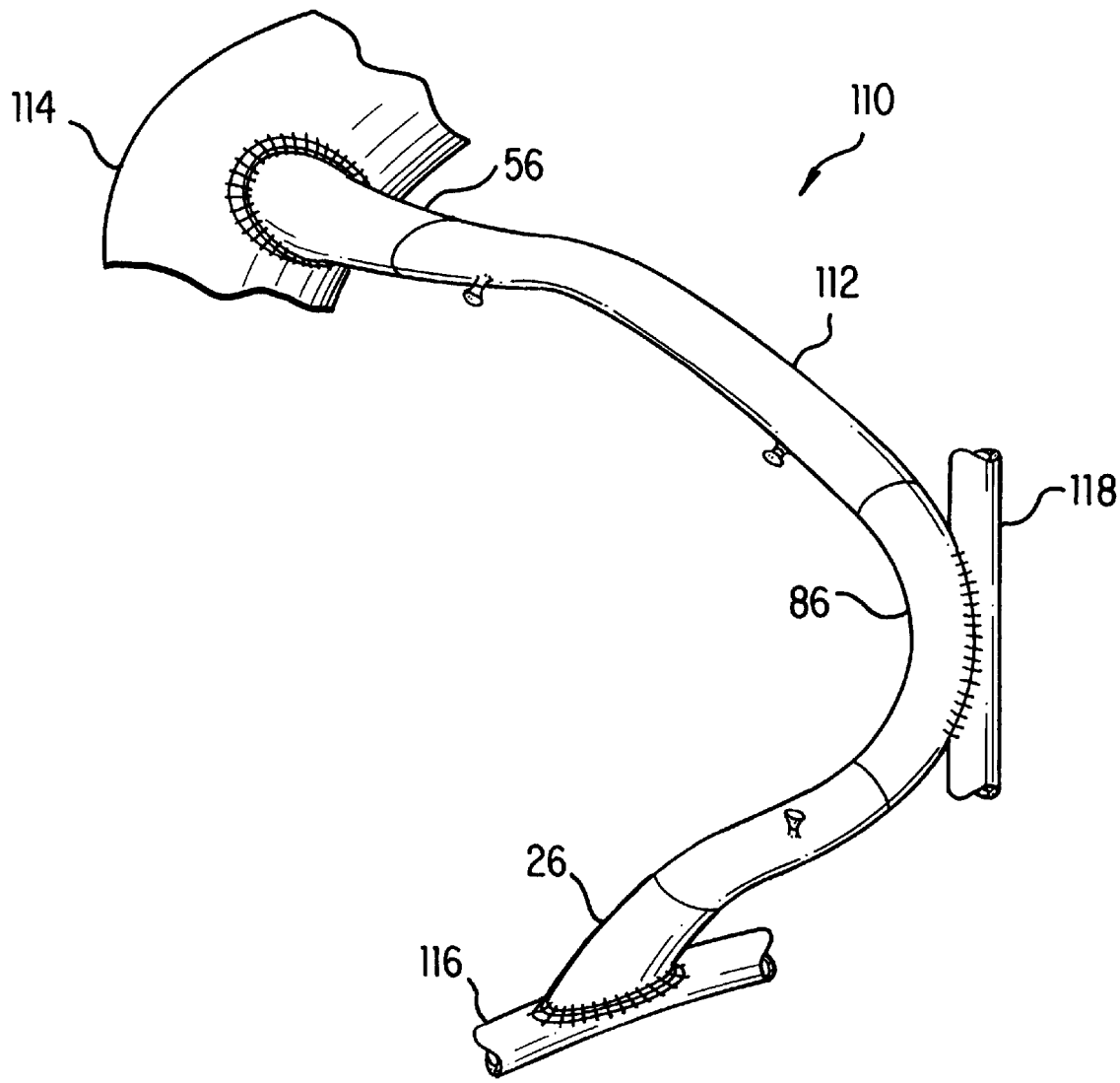
FIG. 9 illustrates a graft system and method according to a fourth embodiment of the present invention.

FIG. 9 illustrates a graft system 110 according to a fourth embodiment of the present invention shown in a coronary artery bypass graft system, in which the principles illustrated in FIGS. 1–8 above are utilized in a single system. The system 110 provides a vein graft 112 that is anastomosed at three locations to an aorta 114 and two arteries 116, 118. A support ring 56, such as the support ring 56 of FIGS. 6A and 6B, is secured to a first end of the vein graft 112, which is anastomosed in an side-to-end manner to the aorta 114. A support ring 26, such as support ring 26 of FIGS. 2A and 2B, is secured to a second end of the vein graft 112, which is anastomosed in an end-to-side manner to an artery 116. A support sleeve 86 is supported at a mid-portion of the vein graft 112, which is anastomosed in a side-to-side manner to another artery 118.

Figure 10A:
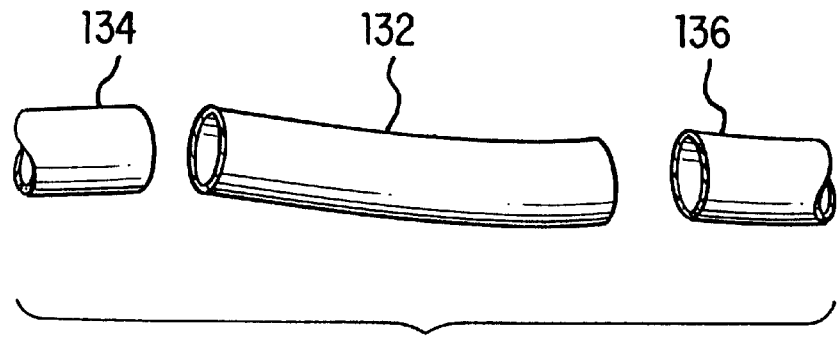
FIGS. 10A–10C illustrate a prosthetic graft system and method according to a fifth embodiment of the present invention shown in use to connect two arteries in an end-to-end manner.
Figure 10B:
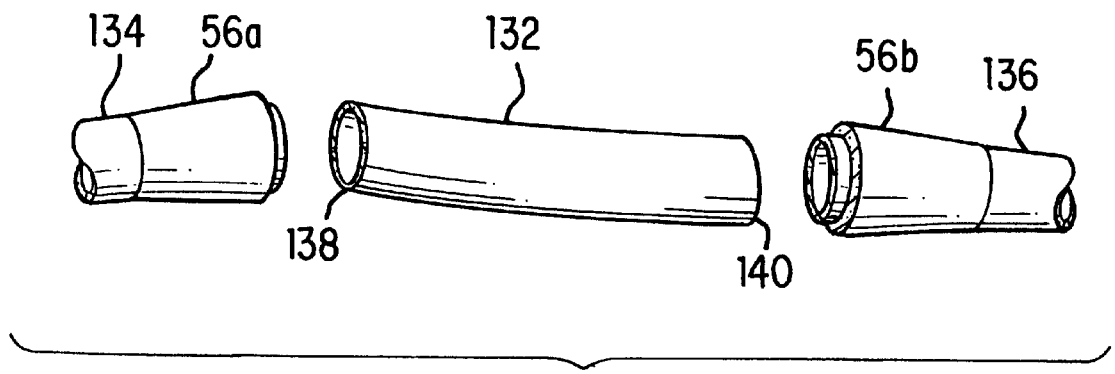
Figure 10C:
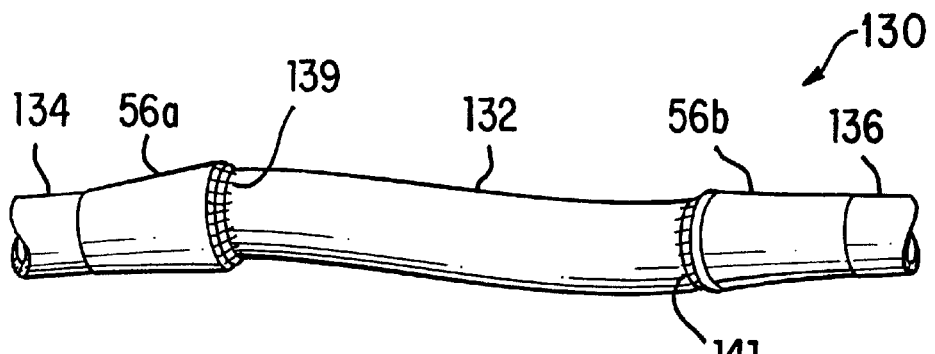

FIGS. 10A–10C illustrate another system 130 according to the present invention, in which a prosthetic graft 132 is used to connect two arteries 134, 136 in end-to-end manner. The system 130 provides a prosthetic graft 132, which is preferably made of a non-expandable material, such as Dacron or ePTFE (polytetrafluoroethylene). Referring to FIG. 10B, a first support ring 56a is slid over the anastomotic end of the first artery 134, and a second support ring 56b is slid over the anastomotic end of the second artery 136. The support rings 56a, 56b can be the same as those described under the designation 56 in FIGS. 6A and 6B. The support rings 56a, 56b are secured to the anastomotic ends of the arteries 134, 136, respectively, by sliding the rings 56a, 56b over the ends in a manner so that the first larger end 62 of the rings 56a, 56b face the anastomotic site (i.e., facing the graft 132) and then applying a stitching (such as the use of guide stitches). The combined first end 62 of the first support ring 56a and the end of the first artery 134 are anastomosed to a first end 138 of the graft 132 by stitches 139. Similarly, the combined first end 62 of the second support ring 56b and the end of the second artery 136 are anastomosed to a second end 140 of the graft 132 by stitches 141.

Thus, as with the other embodiments set forth herein, the graft assembly 130 provides support rings on the weaker ends of the anastomotic sites. In this case, the weaker ends are the arteries 134, 136, since the graft 132 is a prosthetic graft having a structure and material that is stronger or stiffer than the arteries 134, 136. The gradual decreasing thickness of the wall 57 provides the strongest support at the first end 62 of the support ring 56, where the wall 57 has the greatest thickness, and also provides a gradually increasing flexibility (i.e., as the thickness decreases) from the location of the stitches 139, 141 to the uncovered portions of the arteries 134, 136, respectively.

Thus, the support rings 26, 56 and the support sleeve 86 that are used in the graft systems and methods according to the present invention promote optimal anastomosis. The support rings 26, 56 and the support sleeve 86 make it easier for the surgeon to create an optimal anastomosis because they render the graft systems easier to handle and visualize, they provide external circumferential support to the weaker vessel (i.e., either the vein graft or the diseased artery) at the anastomosis site, they provide an effective seal for the anastomosis, and they prevent suture cutting through the vein graft or the diseased artery, thereby minimizing bleeding. In addition, the gradually decreasing wall thickness of the support rings 26, 56 and the support sleeve 86 provides a gradually tapering or withdrawing of the support from the anastomotic coaptation. The support rings 26, 56 and the support sleeve 86 further provide proper contour for the vein graft or arteries, and minimize overstrain, stress, and buckling while maintaining the continuity of the arterial pulse wave propagation. A smooth transition of internal stress and interluminal flow boundary is provided from the anastomotic end (i.e., the thickest end) of the support rings 26, 56 and the support sleeve 86 to the other end, thereby minimizing the possibility of flow boundary separation. This smooth and gradual stress and boundary transition is achieved by the geometry (e.g., tapering and decreasing thickness) of the support rings 26, 56 and the support sleeve 86, and the property transition of the materials of the support rings 26, 56 and the support sleeve 86.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A graft system, comprising:
   a vein graft having a first end and a second end, the first and second ends each adapted to be connected to a host vessel or aorta; and
   a first support ring and a second support ring, each support ring having a generally cylindrical wall having a solid cross-sectional area, and having a thickness and defining a passageway, each ring further including a first end and a second end, with the thickness of the wall of each ring gradually decreasing from the first end of the ring to the second end of the ring;
   wherein the first end of the vein graft is retained inside the passageway of the first support ring with the first end of the first support ring adjacent the first end of the vein graft, and the second end of the vein graft is retained inside the passageway of the second support ring with the first end of the second support ring adjacent the second end of the vein graft.

2. The graft system of claim 1, wherein the vein graft is a host saphenous vein.

3. The graft system of claim 1, wherein the thickness of the wall of the second support ring decreases in a linear manner from the first end of the second support ring to the second end of the second support ring.

4. The graft system of claim 1, wherein the vein graft defines a longitudinal axis, and wherein the first end of the first support ring is disposed at a non-perpendicular angle with respect to the longitudinal axis.

5. The graft system of claim 1, wherein the vein graft defines a longitudinal axis, and wherein the first end of the first support ring is disposed generally perpendicular with respect to the longitudinal axis.

6. The graft system of claim 1, wherein the first end of the vein graft is everted over the first end of the first support ring and stitched thereto.

7. The graft system of claim 1, wherein the first and second support rings are made of an elastic material having sufficient stiffness so that it will not expand beyond a certain limit.

8. A graft system that includes a first host vessel and a second host vessel, each host vessel having an exposed end, the system comprising;

a graft having a first end and a second end; and
   a first support ring and a second support ring, each support ring having a generally cylindrical wall having a solid cross-sectional area, and having a thickness and defining a passageway, each ring further including a first end and a second end, with the thickness of the wall gradually decreasing from the first end of the ring to the second end of the ring;
   wherein the exposed end of the first host vessel is retained inside the passageway of the first support ring with the first end of the first support ring adjacent the exposed end of the first host vessel, and the exposed end of the second host vessel is retained inside the passageway of the second support ring with the first end of the second support ring adjacent the exposed end of the second host vessel; and
   wherein the first end of the graft is attached to the exposed end of the first host vessel, and the second end of the graft is attached to the exposed end of the second host vessel.

9. The graft system of claim 8, wherein the graft is a prosthetic graft.

10. The graft system of claim 8, wherein the thickness of the wall of the second support ring decreases in a linear manner from the first end of the second support ring to the second end of the second support ring.

11. The graft system of claim 8, wherein each host vessel defines a longitudinal axis, and wherein the first end of the first support ring is disposed at a non-perpendicular angle with respect to the longitudinal axis.

12. The graft system of claim 8, wherein each host vessel defines a longitudinal axis, and wherein the first end of the first support ring is disposed generally perpendicular with respect to the longitudinal axis.

13. The graft system of claim 8, wherein the exposed end of the first host vessel is everted over the first end of the first support ring and stitched thereto.

14. The graft system of claim 8, wherein the support rings are made of an elastic material having sufficient stiffness so that it will not expand beyond a certain limit.

15. A graft system, comprising:
   a vein graft having a first end and a second end, the first and second ends each adapted to be connected to a host vessel or aorta; and
   a first support ring and a second support ring, each support ring having a generally cylindrical wall having a thickness and defining a passageway, each ring further including a first end and a second end, with the thickness of the wall of each support ring decreasing in a linear manner from the first end of the ring to the second end of the ring;
   wherein the first end of the vein graft is retained inside the passageway of the first support ring with the first end of the first support ring adjacent the first end of the vein graft, and the second end of the vein graft is retained inside the passageway of the second support ring with the first end of the second support ring adjacent the second end of the vein graft.

16. A graft system, comprising:

a vein graft defining a longitudinal axis and having a first end and a second end, the first and second ends each adapted to be connected to a host vessel or aorta; and a first support ring and a second support ring, each support ring having a generally cylindrical wall having a thickness and defining a passageway, each ring further including a first end and a second end, with the thickness of the wall being greater at the first end than at the second end, and the first end of the first support ring being disposed at a non-perpendicular angle with respect to the longitudinal axis;

wherein the first end of the vein graft is retained inside the passageway of the first support ring with the first end of the first support ring adjacent the first end of the vein graft, and the second end of the vein graft is retained inside the passageway of the second support ring with the first end of the second support ring adjacent the second end of the vein graft.

17. A support ring for use in providing transitional support to an end of either a graft or a host vessel, the support ring comprising:

a generally cylindrical wall having a thickness and defining a passageway that is adapted for receiving an end of a vein graft or an end of a host vessel, the passageway defining a longitudinal axis; and a first end and a second end, with the thickness of the wall being greater at the first end than at the second end, and with first end of the support ring disposed at a non-perpendicular angle with respect to the longitudinal axis.

\* \* \* \* \*